United States Patent [19]

Gorton et al.

[11] 4,001,345

[45] Jan. 4, 1977

[54] DISTILLATION OF METHYLCHLOROFORM

[75] Inventors: Earl M. Gorton, Sulphur; Robert W. Kline, Lake Charles, both of La.

[73] Assignee: PPG Industries, Inc., Pittsburgh, Pa.

[22] Filed: June 2, 1975

[21] Appl. No.: 583,228

[52] U.S. Cl. .................................... 260/652 P
[51] Int. Cl.² ................ C07C 17/38; C07C 19/02
[58] Field of Search ............................ 260/652 P

[56] References Cited

UNITED STATES PATENTS 3,115,528   12/1963   Benner, Jr. et al. ........... 260/652 P
3,647,895   3/1972    Fruhwirth et al. ............. 260/652 P

*Primary Examiner*—D. Horwitz
*Attorney, Agent, or Firm*—Roger S. Benjamin

[57] ABSTRACT

Methylchloroform containing ferric chloride and quaternary ammonium halide is distilled without significant decomposition.

3 Claims, No Drawings

DISTILLATION OF METHYLCHLOROFORM

BACKGROUND OF THE INVENTION

Methylchloroform (1,1,1-trichloroethane) may be produced by Friedel-Crafts catalyzed reactions such as the liquid phase hydrochlorination of vinylidene chloride using a ferric chloride catalyst. The methylchloroform product exiting from the reactor contains a portion of the catalyst which subsequently promotes decomposition upon moderate heating when purification techniques such as distillation are attempted.

It is conventional to conduct vinylidene chloride hydrochlorinations as continuous processes at temperatures of about 38° C., using about 0.1 to 10.0 percent ferric chloride catalyst based on the weight of reaction media (reaction media is usually excess methylchloroform).

Principal contaminants in the reaction product are relatively volatile hydrogen chloride and vinylidene chloride together with non-volatile catalyst. All of these contaminants are readily separated from the methylchloroform product by distillative techniques. The distillative procedure is usually conducted in stages and in normal operations some small transfer of catalyst from stage to stage is experienced. In addition, unreacted hydrogen chloride contained in the product stream corrodes the distillation apparatus and tends to form a scale of metal salts which accumulate in the distilland with a deleterious destabilizing effect.

SUMMARY OF THE INVENTION

This invention concerns the distillation of methylchloroform containing ferric chloride catalyst without significant methylchloroform decomposition. It involves performing the distillation of methylchloroform containing ferric chloride in the presence of methylchloroform soluble quaternary ammonium halide.

DETAILED DESCRIPTION OF THE INVENTION

Methylchloroform Distillation

Distillation of methylchloroform product containing ferric chloride catalyst may be conducted at either superatmospheric, atmospheric, or sub-atmospheric pressures using one or more distillation units. Typical practice is to run the reactor output to a flash distillation zone operated at about or slightly above atmospheric pressure (74°–80° C.), then take the methylchloroform overhead of the flash distillation zone to a stripper zone operated at higher superatmospheric pressure (over 94° C.) to remove "lights", then route the bottoms of the stripping zone to a topping still (74°–80° C.) for removal of purified methylchloroform as overhead.

Distillation is usually conducted at temperatures considerably higher than the reactor temperature, typically in excess of 74° C. Therefore, it is especially important that the methylchloroform product be stabilized at a point where it begins its passage through the distillative procedure. Stabilization is achieved by adding methylchloroform soluble quaternary ammonium halide inhibitor to the methylchloroform product. Since Friedel-Crafts catalysts (especially, FeCl₃) are constantly present either as reactor waste or corrosion by-products, the quaternary ammonium halide should be present wherever in the distillative purification procedure the methylchloroform is subjected to elevated temperatures in the presence of ferric chloride.

The quaternary ammonium halide must be dissolved in the methylchloroform to be effective in inhibiting its decomposition. If desired, the quaternary ammonium halide may be pre-dissolved and added to the methylchloroform in the form of a solution. Alternately, the quaternary ammonium halide may be added as a solid under conditions of sufficient agitation to assure its solution. If desired, one or more quaternary ammonium halide may be used in combination.

This process may be operated by continuous or intermittent introduction of the quaternary ammonium halide at one or more points in each piece of the distillation apparatus. Quaternary ammonium halide introduced into the upper rectification zone of a column will tend to migrate to the bottoms as a non-volatile component, but its temporary presence in the upper section of the column will be effective in suppressing methylchloroform decomposition at that location.

The quaternary ammonium halide containing bottoms fraction of any distillation zone may be rerouted to other distillation zones to permit effective reuse of the accumulated quaternary ammonium halide.

Quaternary Ammonium Halide Stabilizer

"Quaternary ammonium halides" useful in the practice of this invention are those which are sufficiently soluble in methylchloroform and are represented by the formula:

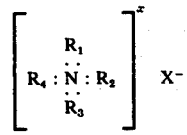

where
R₁, R₂, R₃ and R₄ may be the same or different and are selected from methyl radicals, or alkyl and alkenyl radicals of 7 to 20 carbon atoms, provided that at least one and no more than two members of the group R₁, R₂, R₃ and R₄ are methyl radicals; and X is bromine, iodine or chlorine.

Quaternary methyl ammonium halides having the requisite methylchloroform solubility possess two or more long chain alkyl or alkenyl groups of 7 to 20 carbon atoms. Quaternary methyl ammonium halides having three long chain alkyl groups of 7 to 20 carbon atoms are especially preferred. Illustrative compounds useful in the practice of this invention are tricaprylyl methyl ammonium chloride, tricaprylyl methyl ammonium bromide, dioctadecyl dimethyl ammonium chloride, tridodecyl methyl ammonium chloride and dioctadecenyl dimethyl ammonium bromide.

It has been found that in order to effectively resist decomposition of the methylchloroform by the ferric chloride the quaternary ammonium halide should be present to the extent of at least about 2 moles of quaternary ammonium halide per mole of ferric chloride and preferably in the range of 2 to 4 moles per mole of ferric chloride. There is no upper limit to the useable mole ratio of quaternary ammonium halide to ferric chloride other than that required by convenience and cost.

The minimum extent to which the quaternary ammonium halide inhibitor must be "methylchloroform soluble" is determined on the basis of the anticipated ferric chloride concentration in the region where protection against decomposition is desired. For example, if the ferric chloride concentration in the initial flash distillation stage is 0.2 mole percent, then the soluble quaternary ammonium halide must be sufficiently soluble to achieve a concentration of about 0.4 mole percent. Usually the ferric chloride concentration encountered in the methylchloroform will range from 0.1 to 10.0 weight percent in the initial reactor output and decrease to 0.01 or trace amounts in the final distillation stages.

EXAMPLE I

This example illustrates the decomposition of methylchloroform containing a high concentration of ferric chloride catalyst when no inhibitor is present. In a 2,000 milliliter Parr stainless steel air stirred pressure reactor was placed 1342.5 grams of methylchloroform and 42.2 grams (0.26 moles) $FeCl_3$, to give a 3.14 weight percent ferric chloride mixture based on the weight of methylchloroform. The temperature of reaction was gradually raised from 13° C. to 105° C. as shown in Table 1, below. Pressure rise in excess of the normal vapor pressure of methylchloroform is regarded as evidence of decomposition, due to the evolution of the volatile hydrogen chloride and vinylidene chloride decomposition products. All proportions are given on a weight basis.

Table 1

| Time Min. | Temp. ° C. | Pressure Pascals × 10⁻⁵ |
| --- | --- | --- |
| 0 | 13 | 1.22 |
| 10 | 22 | 1.57 |
| 20 | 50 | 3.91 |
| 30 | 88 | 11.01 |
| 40 | 95 | 14.80 |
| 50 | 105 | 16.87 |
| 60 | 105 | 17.22 |

The vapor pressure of methylchloroform at 100° C. is 2.14 × 10⁵ pascals.

EXAMPLE II

This example was conducted using the apparatus of Example I. 41.3 grams (0.255 moles) of $FeCl_3$ were added to 1313 grams of methylchloroform to give a 3.14 weight percent ferric chloride containing mixture. 223.8 grams (0.506 moles) of ALIQUAT-336[1] were dissolved in the mixture, The temperature of reaction was gradually raised from 17° C. to 102° C. as shown in Table 2 below.

Table 2

| Time Min. | Temp. ° C. | Pressure Pascals × 10⁻⁵ |
| --- | --- | --- |
| 0 | 17 | 1.01 |
| 20 | 60 | 2.53 |
| 30 | 90 | 3.08 |
| 40 | 100 | 3.63 |
| 50 | 102 | 3.63 |
| 60 | 100 | 3.56 |
| 70 | 96 | 3.43 |
| 125 | 98 | 3.56 |
| 175 | 99 | 3.91 |
| 240 | 96 | 3.91 |

[1]ALIQUAT-336 is a water insoluble quaternary salt made by methylation of straight chain saturated symmetrical tertiary amine, where the straight chains are a mixture of $C_8$ and $C_{10}$ carbon atoms with $C_8$ predominating and the average molecular weight is 442.

From this example, it can be seen that quaternary ammonium halides exhibit a pronounced tendency to control the decomposition of methylchloroform in the presence of ferric chloride.

It is to be understood that although the invention has been described with specific references and specific details of embodiments thereof, it is not to be so limited since changes and alterations therein may be made which are within the full intended scope of this invention as defined by the appended claims.

We claim:
1. An improved method of purifying methylchloroform containing ferric chloride which comprises dissolving in the methylchloroform at least about two moles of quaternary ammonium halide represented by the formula:

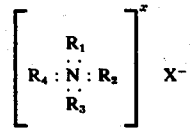

where
$R_1$, $R_2$, $R_3$ and $R_4$ may be the same or different and are selected from methyl radicals, or alkyl and alkenyl radicals of 7 to 20 carbon atoms, provided that at least one and no more than two members of the group $R_1$, $R_2$, $R_3$ and $R_4$ are methyl radicals; and
X is bromine, iodine or chlorine,
per mole of ferric chloride and distilling methylchloroform therefrom.

2. The method of claim 1 wherein two to four moles of quaternary ammonium halide are present per mole of ferric chloride.

3. The method of claim 1 wherein the quaternary ammonium halide is tricaprylyl methyl ammonium chloride.

* * * * *